(12) United States Patent
Douce et al.

(10) Patent No.: US 10,049,866 B2
(45) Date of Patent: Aug. 14, 2018

(54) IN-SOURCE CHEMICAL MODIFICATION OF NON POLAR ANALYTES USING ATMOSPHERIC PRESSURE CHEMICAL IONISATION SOURCE

(71) Applicant: Micromass UK Limited, Wilmslow (GB)

(72) Inventors: David Douce, Congleton (GB); Gareth R. Jones, Altrincham (GB)

(73) Assignee: MICROMASS UK LIMITED, Wilmslow (GB)

( * ) Notice: Subject to any disclaimer, the term of this patent is extended or adjusted under 35 U.S.C. 154(b) by 0 days.

(21) Appl. No.: 15/487,537

(22) Filed: Apr. 14, 2017

(65) Prior Publication Data

US 2017/0301530 A1 Oct. 19, 2017

(30) Foreign Application Priority Data

Apr. 15, 2016 (GB) .................................. 1606598.9

(51) Int. Cl.
| | |
|---|---|
| *H01J 49/14* | (2006.01) |
| *H01J 49/00* | (2006.01) |
| *G01N 27/62* | (2006.01) |
| *G01N 30/72* | (2006.01) |

(52) U.S. Cl.
CPC .......... *H01J 49/145* (2013.01); *G01N 27/622* (2013.01); *G01N 30/7206* (2013.01); *H01J 49/0031* (2013.01); *H01J 49/0045* (2013.01)

(58) Field of Classification Search
USPC ................................................. 250/288, 282
See application file for complete search history.

(56) References Cited

U.S. PATENT DOCUMENTS

| | | | |
|---|---|---|---|
| 7,041,972 B2 | 5/2006 | Bajic et al. | |
| 7,153,694 B2 | 12/2006 | Evans et al. | |
| 9,070,540 B2 | 6/2015 | Brown et al. | |
| 9,105,458 B2 | 8/2015 | Trimpin et al. | |
| 2011/0294767 A1* | 12/2011 | Gedulin ............... | A61K 9/0031 514/171 |
| 2013/0122599 A1 | 5/2013 | Brown et al. | |
| 2013/0281580 A1* | 10/2013 | Malofsky ............. | C08F 122/14 524/46 |
| 2015/0144782 A1 | 5/2015 | Fogwill et al. | |

\* cited by examiner

*Primary Examiner* — Kiet T Nguyen
(74) *Attorney, Agent, or Firm* — Womble Bond Dickinson (US) LLP; Deborah M. Vernon; Heath T. Misley

(57) ABSTRACT

A method for analyzing an aliphatic compound by mass spectrometry which comprises: (i) ionizing an aliphatic compound in the presence of a heterocyclic modifier; and (ii) mass analyzing the resulting ions to obtain mass spectrometric data.

24 Claims, 11 Drawing Sheets

US 10,049,866 B2

IN-SOURCE CHEMICAL MODIFICATION OF NON POLAR ANALYTES USING ATMOSPHERIC PRESSURE CHEMICAL IONISATION SOURCE

CROSS-REFERENCE TO RELATED APPLICATION

This application claims priority from and the benefit of United Kingdom patent application No. 1606598.9 filed on 15 Apr. 2016. The entire content of this application is incorporated herein by reference.

FIELD OF THE INVENTION

The present invention relates to modifiers for use in ionisation processes for mass spectrometry, in particular to the use of heterocyclic modifiers in the analysis of aliphatic hydrocarbons by atmospheric pressure chemical ionisation mass spectrometry for gas chromatography (APCI-GC).

BACKGROUND

There are currently very few ionisation sources capable of providing a simple mass spectrum for non-polar aliphatic chemicals including alkanes, alkenes and alkynes from a GC inlet. High energy electron impact (electron ionisation) provides considerable fragmentation data but little molecular ion information. Field ionisation and field desorption have also been used for the characterisation of paraffins and olefins within crude oil or fractions thereof. However, the carbon dendrite filaments used in these methods can be very fragile, leading to a lack of robustness and reducing the number of samples that can be analysed before the filaments need replacing. In addition, the carbon dendrites can degrade during the acquisition resulting in irreproducibility in response.

Atmospheric pressure chemical ionisation (APCI) is an ionisation method used in mass spectrometry which utilises gas-phase ion-molecule reactions at atmospheric pressure to produce ions from an analyte which are then analysed by mass spectrometry. APCI is based on a coronal discharge process. There are two main potential ionisation mechanisms: nitrogen charge transfer (producing predominantly a radical cation) and protonation (resulting in a protonated molecular ion). The dominant ionisation process can be defined by the environment, which is ultimately controlled by the user.

Certain types of molecules including aliphatic molecules such as paraffins, isoparaffins and olefins do not consistently ionise by the expected routes. Paraffins for example have been shown to undergo hydride abstraction to form $[M-H]^+$ in addition to formation of nitrogen/carbon/oxygen adducts including $[M+N]^+$ and $[M+CH_4N_2]^+$ in addition to some useful backbone fragmentation. The result is a complex mass spectrum which may be difficult to interpret without prior knowledge. Results may be inconsistent, as different mass spectrometers or environments may give rise to different spectra for the same compounds. For example, the same type of molecules can undergo different ionisation processes depending upon the gas flow, gas composition and temperature of the environment during the ionisation process. In one example, it has been found that APCI-GC analysis of the alkane hexatriacontane ($C_{36}H_{74}$) can show three dominant ions in the spectrum including the hydride abstracted $[M-H]^+$ (M-1), in addition to an $[M-H+N]^+$ (M+13) adduct and a $[M+NOH_2]^+$ (M+32) base peak. However, the relative abundances of these adducts can vary significantly depending on subtle changes within the source environment (e.g. gas composition, velocity or temperature).

Water and alcohols have been used as modifiers or dopants to induce protonation during atmospheric pressure chemical ionisation of polar molecules. However, the presence of water can further complicate the mass spectra of aliphatic compounds through the formation of adducts. There therefore remains a need to improve the analysis of aliphatic molecules by mass spectrometry.

SUMMARY

The present inventors have now found that the analysis of aliphatic molecules by mass spectrometry can be improved if the ionisation takes place in the presence of a heterocyclic modifier. In particular, the resulting mass spectra may be simpler and hence easier to interpret, and/or they may be more consistently produced.

The modifiers may be used in a variety of ionisation processes, but they find particular application in atmospheric pressure chemical ionisation mass spectrometry for gas chromatography (APCI-GC).

There is therefore provided use of a heterocyclic compound as a modifier during ionisation of an aliphatic compound for mass spectral analysis.

There is also provided a method for analysing an aliphatic compound by mass spectrometry which comprises:
(i) ionising an aliphatic compound in the presence of a heterocyclic modifier; and
(ii) mass analysing the resulting ions to obtain mass spectrometric data.

The ionisation is preferably atmospheric pressure chemical ionisation (APCI), atmospheric pressure photoionisation (APPI), or APCI/APPI mixed mode ionisation. The use and method may involve GC-MS, LC-MS or SFC-MS. GC-MS is particularly beneficial due to its suitability for the analysis of non-polar compounds.

DETAILED DESCRIPTION

The present invention involves the use of heterocyclic modifiers to improve the mass spectra of aliphatic molecules (analytes), particularly non-polar aliphatic molecules. It finds particular utility in atmospheric pressure chemical ionisation mass spectrometry for gas chromatography (APCI-GC).

As used herein, improving a mass spectrum refers to simplifying the mass spectrum, and/or improving consistency of the spectra for the same analytes over time or between different spectrometers and/or making the mass spectrum easier to interpret.

The following abbreviations are used herein:
APCI atmospheric pressure chemical ionisation
APPI atmospheric pressure photoionisation
GC gas chromatograph
LC liquid chromatograph
SFC supercritical fluid chromatograph
2D two dimensional Mass spectrometers comprising atmospheric pressure chemical ionisation (APCI), atmospheric pressure photoionisation (APPI), or APCI/APPI mixed mode ionisation sources are well known in the art. They may be coupled to gas chromatographs (GC), liquid chromatographs (LC) or supercritical fluid chromatographs (SFC) as inlet means. For example, US2005/0035286 discloses a mass spectrometer coupled to an APCI source chamber and with a gas or liquid chromatograph as inlet means.

Figure 1:
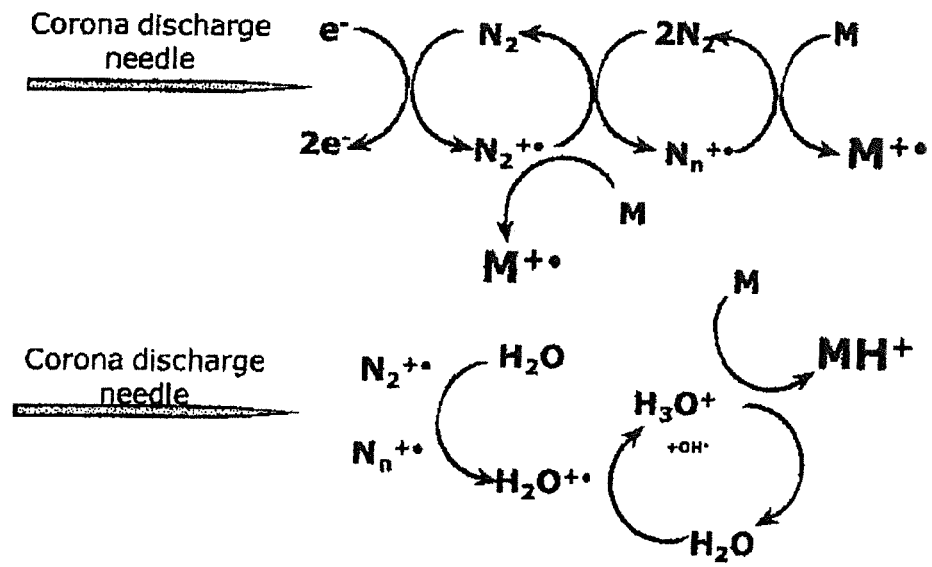
FIG. 1 shows the main ionisation mechanisms in APCI.

Atmospheric pressure chemical ionisation mass spectrometry for gas chromatography (APCI-GC) is often used for the analysis of non-polar or low polarity compounds. In such a system, a gas chromatograph (GC) effluent is released into an ambient atmospheric pressure chemical ionisation (APCI) chamber for the ionisation of non-polar and low polarity compounds. The ionisation process is based on a coronal discharge which can result in two discrete methods of ionisation. These include nitrogen charge transfer (producing predominantly a radical cation) and protonation (resulting in a protonated molecular ion), as shown in FIG. 1. Both of these mechanisms are initiated by the ionisation of molecular nitrogen by an electron.

The field gradient in close proximity to the tip of a corona pin, with a positive voltage applied to it, can be high enough such that an electron can gain sufficient energy to liberate another electron from nitrogen gas molecules with which it collides. As these liberated electrons are already within a very high electrical field gradient, there is a high probability that these will liberate further electrons in subsequent collisions with nitrogen molecules, and thus an electron avalanche is initiated. These reactions also result in nitrogen molecule radical cations, which are repelled away from the pin. The high energy photons produced in these collisions (and through recombination reactions), can escape the electric field and thereby initiate more avalanches by liberating electrons from neutral nitrogen molecules further away from the pin. In this fashion, a corona discharge is a feedback mechanism and can sustain itself once initiated. The high energy photons are also responsible for the characteristic white/purple glow of a corona.

The dominant ionisation process is heavily dependent upon the environment within the atmospheric pressure ionisation chamber and the surrounding environment.

Figure 2:
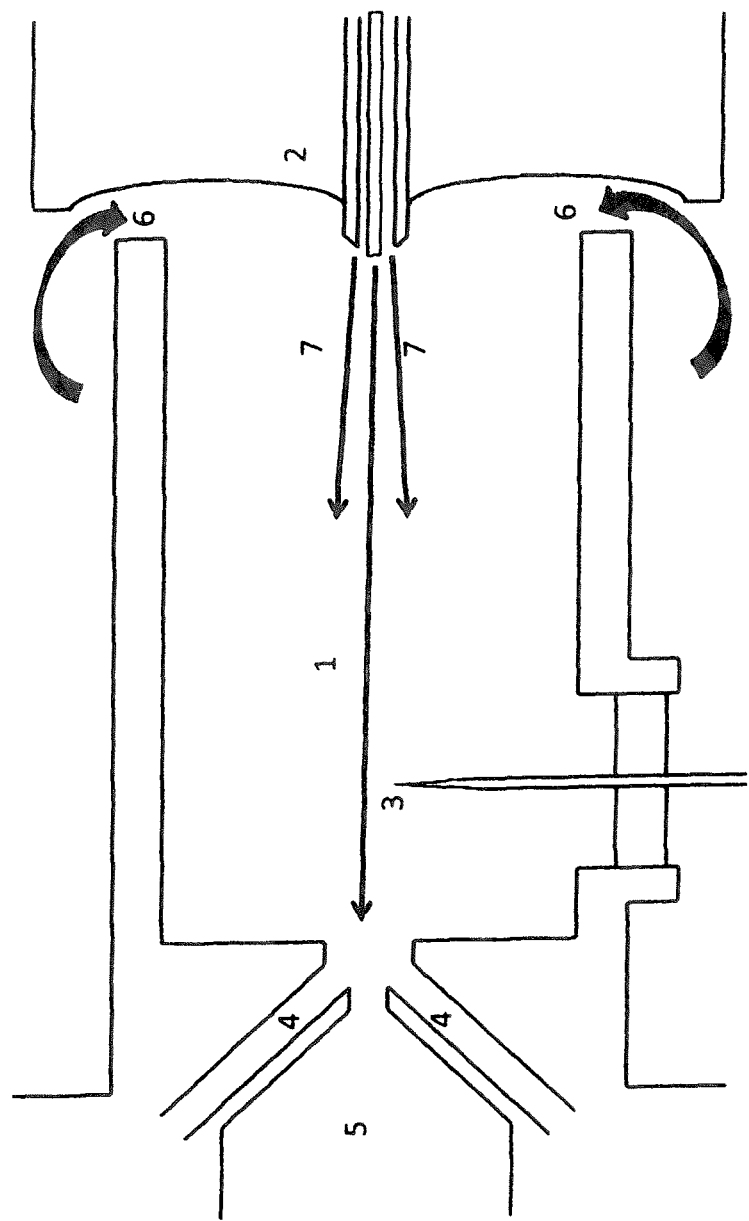
FIG. 2 shows the basic outline of an APCI-GC source chamber.

FIG. 2 shows the basic outline of an APCI-GC source chamber. GC gas effluent enters the chamber environment 1, through the heated transfer line 2. The gas phase analyte molecules traverse the chamber and are ionised in close proximity to the corona located at the tip of the corona pin 3. The environment at this point is highly dependent upon the cone gas flow 4, as this defines the exposed vacuum from the vacuum region 5. For example, if the cone gas flow is low, the vacuum exposed is significant and gas is pulled in from outside the chamber 6, which can potentially pull in moisture/modifier resulting in protonation/adduction. If the cone gas flow is higher (balanced) little or no extra gas flow is required from outside the ionisation chamber, resulting in a dominant charge transfer process. The auxiliary gas flow 6 and make-up gas flow 7 can also have an effect on ionisation, but this effect is less significant than the cone gas flow.

Alkanes and alkenes have been found to ionise differently by APCI depending upon the source environment (corona environment) they are exposed to resulting in an inconsistent ionisation process and hence a range of ions/ion reaction products being observed. It has now been found that the addition of heterocyclic modifiers during APCI of aliphatic compounds can simplify the potential atmospheric adduction processes occurring in the coronal region, reproducibly providing a heterocyclic adduct, predominantly, as a base peak in the resulting mass spectra. In particular, the addition of a heterocyclic modifier results in adduction of the modifier molecule to the ion resulting from hydride abstraction from the analyte giving rise to a $[(M-H)+\text{modifier}]^+$ base peak. For example, if the modifier is pyrrole, the base peak is $[(M-H)+C_4H_5N]^+$. The mass spectrum also generally contains the hydride abstraction ion in addition to useful backbone fragmentation data.

The fact that the heterocycle adducted $[M-H]^+$ ion appears consistently as the base peak in the mass spectra of the aliphatic compounds results in a simplified ionisation profile resulting in a simplified method of identification. In addition, extra mass and fragmentation data is produced which assists in confirming the identity of the analyte. In particular, structurally similar alkanes and alkenes can be distinguished from one another through use of a heterocyclic modifier.

A heterocyclic modifier can also be used in conjunction with other known methods to give further useful information, particularly during analysis of complex mixtures of compounds. For example, initial chromatography separation such as 2D-GC or 2D-LC can help separate components from a mixture and provide information regarding retention times. Alternatively or additionally, ion mobility separation can be carried out on the ions before they are analysed by time of flight mass spectrometry. Ion mobility separation can potentially assist in distinguishing between isomeric compounds, for example branched and straight chain hydrocarbons of the same empirical formula, due to their different ion mobilities, particularly where the formation of adducts with the modifier changes the collisional cross section (CCS) of the original analyte(s). Spectrometers comprising ion mobility cells are well known in the art and are commercially available.

Structural information regarding branching and the position of unsaturation can also be derived from MS/MS (tandem mass spectrometry) studies on particular ions, for example the hydride abstracted modifier adduct ion. For example, fragments showing progressive loss of $CH_2$ (14 m/z) demonstrate the aliphatic nature of the molecule, with changes in the distribution possibly identifying potential sites of unsaturation.

Further information, particularly for complex mixtures, may be obtained by comparing mass spectra obtained with and without the modifier. Additional information may also be obtained through comparing spectra using different heterocyclic modifiers through preferential adduction.

Use of heterocyclic modifiers during the ionisation process has been found to result in mass spectra which are easier to interpret, thus leading to easier identification of aliphatic molecules. Use of heterocyclic modifiers may also improve the consistency of the mass spectra obtained, allowing for more reliable comparison of spectra produced at different times or using different instruments.

Use of heterocyclic modifiers is particularly beneficial in the mass spectral analysis of aliphatic molecules which are difficult to analyse consistently by other techniques. Aliphatic molecules (analytes) which may be analysed using heterocyclic modifiers include non-cyclic hydrocarbons such as alkanes, alkenes and alkynes, all of which may be straight chain or branched. The aliphatic molecules may be non-polar. Beneficially, they contain only carbon and hydrogen atoms. Such hydrocarbons include $C_5$ to $C_{120}$ hydrocarbons, for example $C_{10}$ to $C_{50}$ hydrocarbons.

Variations in the potential ionisation process of alkanes, particularly longer chains alkanes (paraffins) which are known to be of major importance in the oil industry, makes these compounds difficult to identify easily using a corona based ionisation process such as APCI. The present invention may therefore find particular utility in analysing crude oil or fractions thereof which may contain complex mixtures of organic compounds. For example, analysis of the composition and structure of the aliphatic hydrocarbons in a particular sample can provide useful information to a company prospecting for oil.

Suitable modifiers for use herein include mono-, bi-or tricyclic heterocyclic compounds containing carbon atoms and 1-4 heteroatoms. It is postulated that the presence of a heteroatom promotes adduction to the analyte. The heteroatoms may be selected from oxygen, sulphur and/or nitrogen. Such heterocyclic compounds may be aromatic, saturated or partially saturated.

Monocyclic modifiers may be beneficial as they are less likely to suffer from steric hindrance which may limit adduct formation with the analyte.

For ease of handling, it is beneficial that the modifiers are liquid under standard conditions of temperature and pressure. Volatile liquid modifiers are particularly beneficial as they require less energy to transfer them into the gas phase prior to or following introduction into the ionisation chamber.

Examples of suitable modifiers include oxetane, azetidine, thietane, pyrrole, furan, tetrahydrofuran, thiophene, tetrahydrothiophene (thiolane, thiophane), indole, benzothiophene, benzofuran (coumarone), dioxane, piperazine, thiane, dithiane, pyrrolidine, pyridine, pyrimidine, pyrazine, pyran, thiopyran, piperadine, tetrahydropyran, imidazoline, imidazole, pyrazole, oxazole, thiazole, isoxazole, triazole, tetrazole, quinoline, isoquinoline, purine, dibenzofuran and dibenzothiophene, and alkylated derivatives thereof. Suitable alkylated derivatives include $C_{1-6}$ alkylated derivatives, preferably methylated and ethylated derivatives. Such compounds are available commercially.

A beneficial modifier is pyrrole.

The heterocyclic modifiers are generally introduced into an ionisation chamber, for example an atmospheric pressure chemical ionisation chamber or an atmospheric pressure photoionisation chamber, in gaseous form. In APCI-GC, the modifier may be introduced into the ionisation chamber via the auxiliary gas flow 6 (FIG. 2).

The amount of modifier required will depend in part on the sample being analysed and the mode of ionisation. A skilled person will readily be able to vary the amount of modifier to promote adduction rather than charge transfer during the ionisation process and to obtain the best mass spectral results.

Heterocyclic modifiers may also be used during atmospheric pressure photoionisation (APPI) of aliphatic molecules or in mixed mode APCI/APPI. In APPI, ionisation is initiated by high energy photons. However, the sensitivity of APPI-MS is often low. It is believed that use of heterocyclic modifiers can increase the sensitivity of APPI mass spectrometry.

The method may be further illustrated by the following, non-limiting examples.

EXAMPLES

Example 1 (Comparative)

Figure 3:
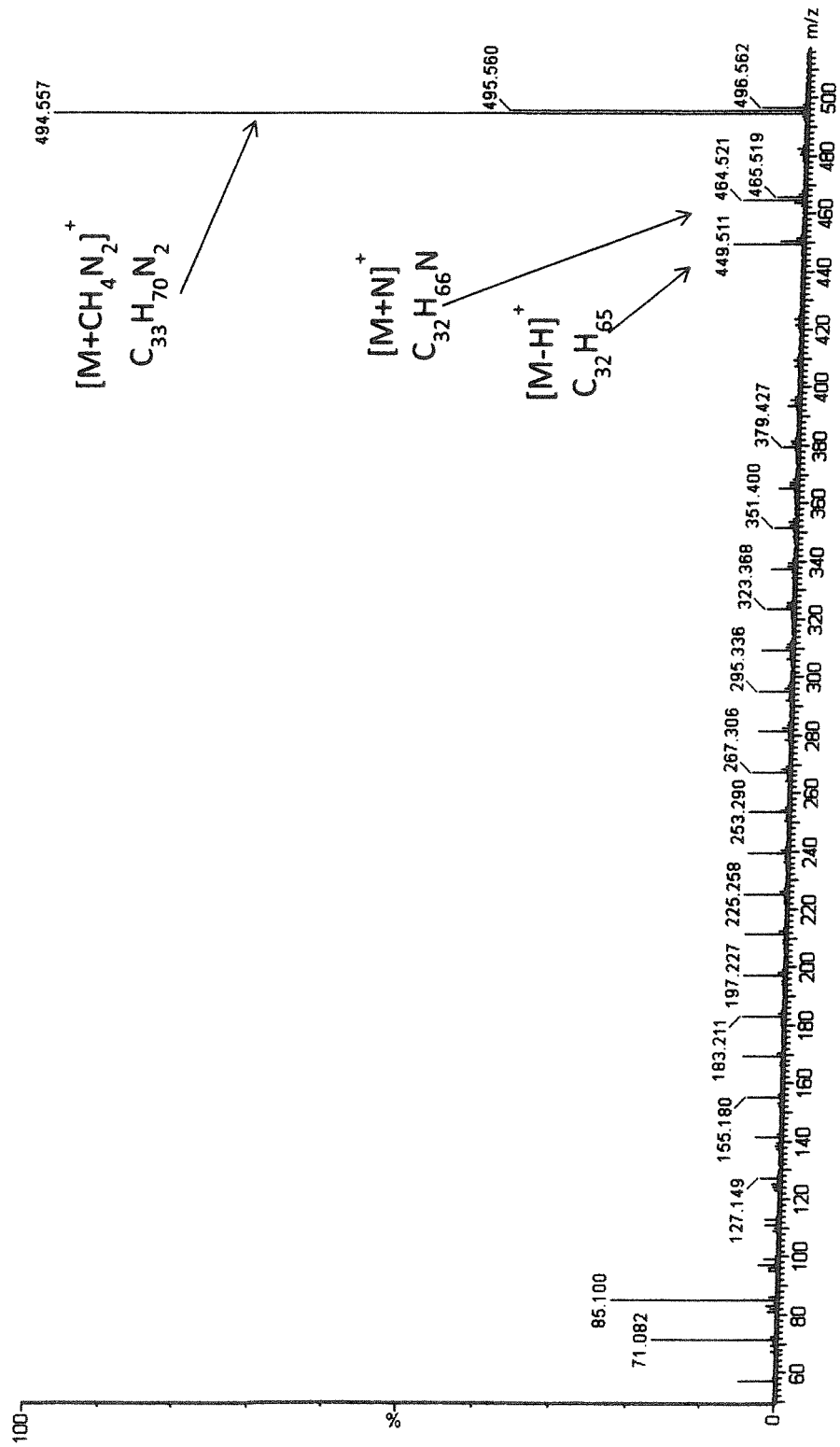
FIG. 3 shows the mass spectrum produced by APCI-GC analysis of dotriacontane ($C_{32}H_{66}$) using a prior art atmospheric pressure chemical ionisation method.

FIG. 3 shows the mass spectrum produced from dotriacontane ($C_{32}H_{66}$) using conventional APCI-GC, without use of a heterocyclic modifier. Ions observed in the spectrum include the hydride abstracted ion, $[M-H]^+$ (M−1), an $[M+N]^+$ (M+14) nitrogen adduct and an $[M+CH_4N_2]^+$ (M+44) base peak.

Example 2 (Comparative)

Figure 4:
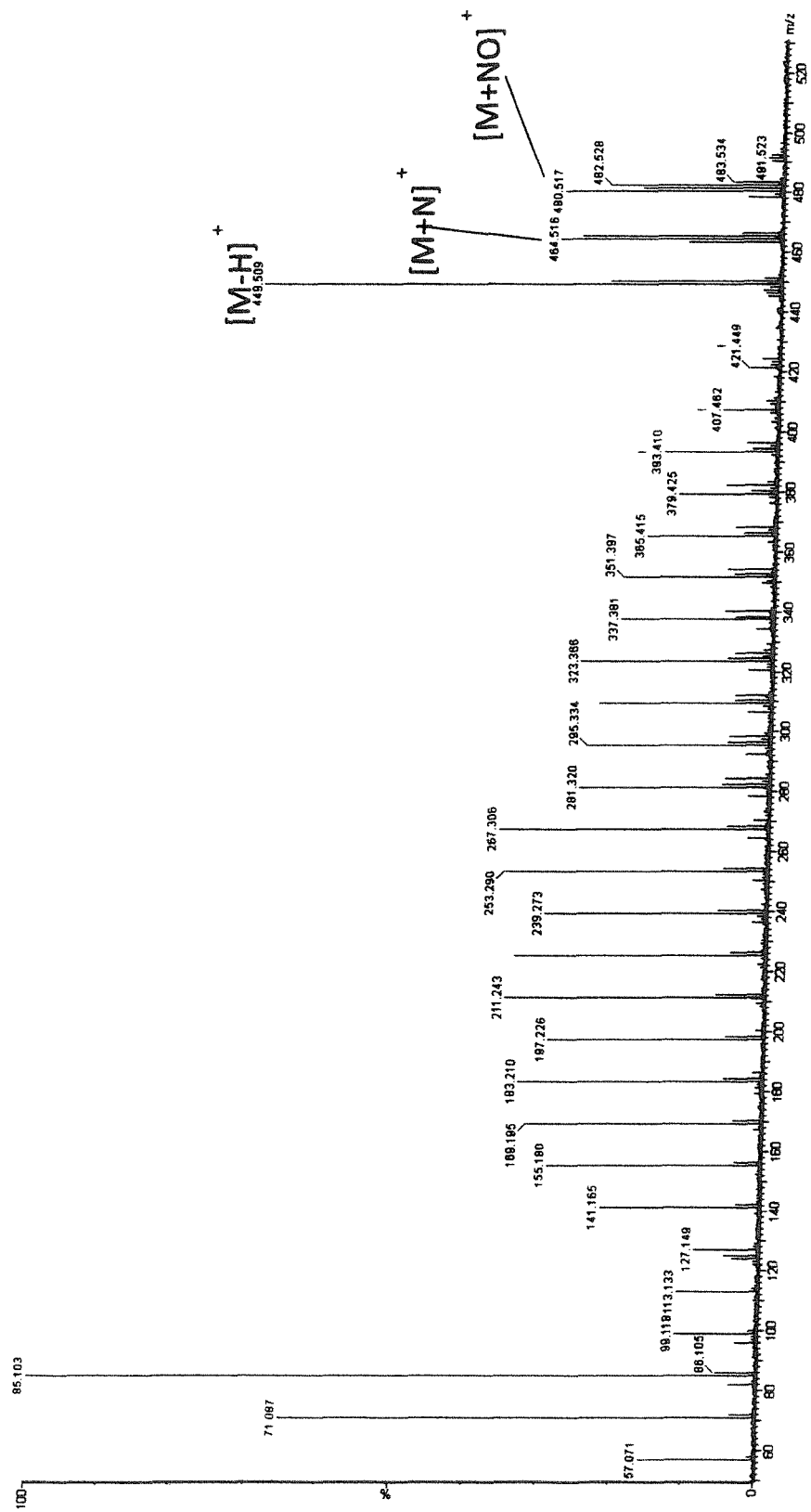
FIG. 4 shows another mass spectrum produced by APCI-GC analysis of dotriacontane ($C_{32}H_{66}$) using a prior art atmospheric pressure chemical ionisation method.

An alternative ionisation profile for an alkane molecule can be seen in FIG. 4. Here the alkane dotriacontane ($C_{32}H_{66}$) shows three dominant ions in the spectrum which include the hydride abstracted ion $[M-H]^+$ (M−1) in addition to an $[M+N]^+$ (M+14) nitrogen adduct and a $[M+NO]^+$ (M+30) base peak. A comparison of FIGS. 3 and 4 demonstrates the difficulties with analysing mass spectra of alkanes due to inconsistent ionisation profiles.

Example 3 (Comparative)

Figure 5:
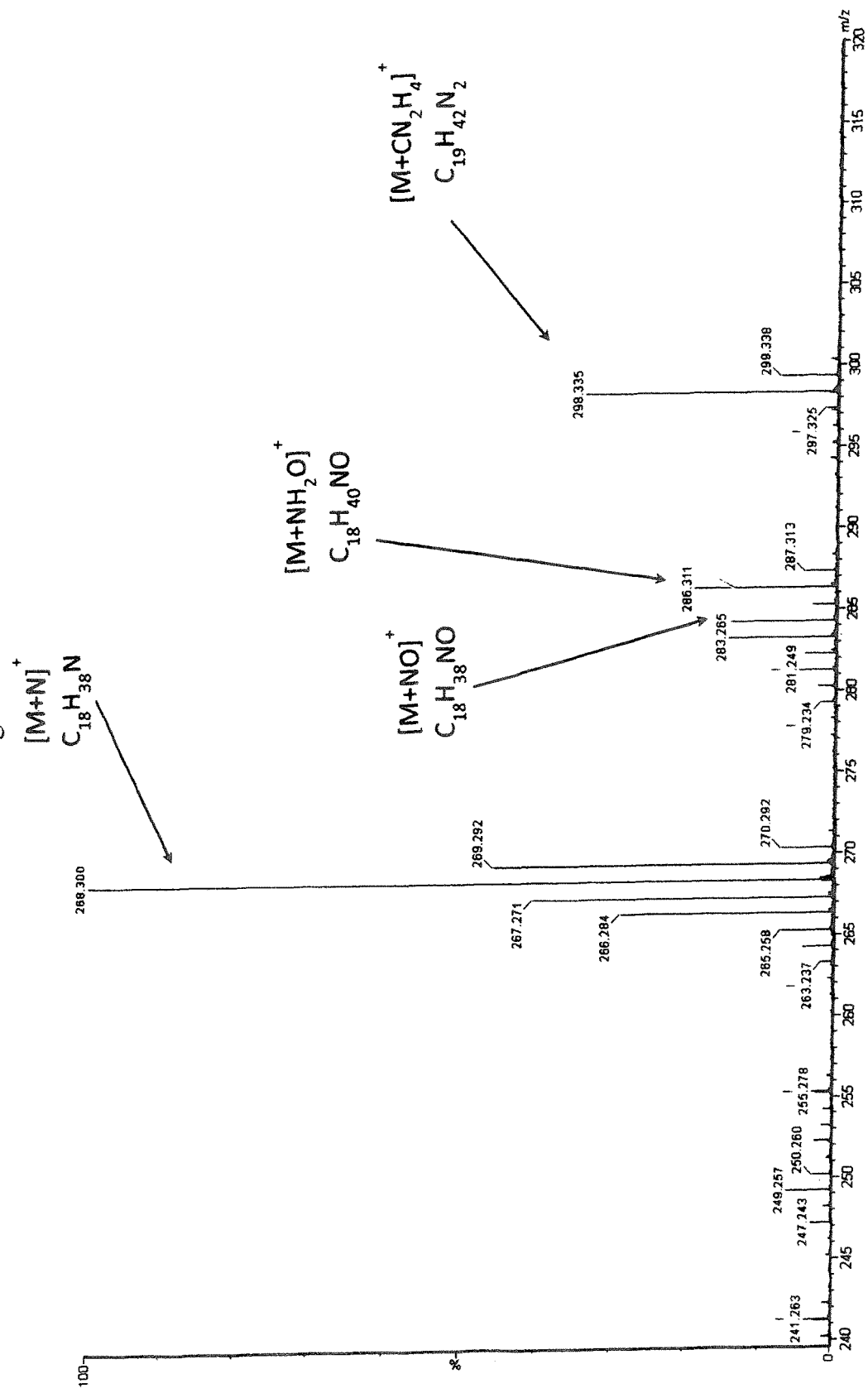
FIG. 5 shows a mass spectrum produced by APCI-GC analysis of octadecane ($C_{18}H_{26}$) using a prior art atmospheric pressure chemical ionisation method.

An additional ionisation profile for another alkane molecule can be seen in FIG. 5. Here the alkane octadecane ($C_{18}H_{38}$) shows a dominant base peak of the $[M+N]^+$ (M+14) nitrogen adduct in addition to an $[M+NO]^+$ (M+30), an $[M+NH_2O]^+$ (M+32) and an $[M+CN_2H_4]^+$ M+44) adduct.

Example 4 (Comparative)

Figure 6:
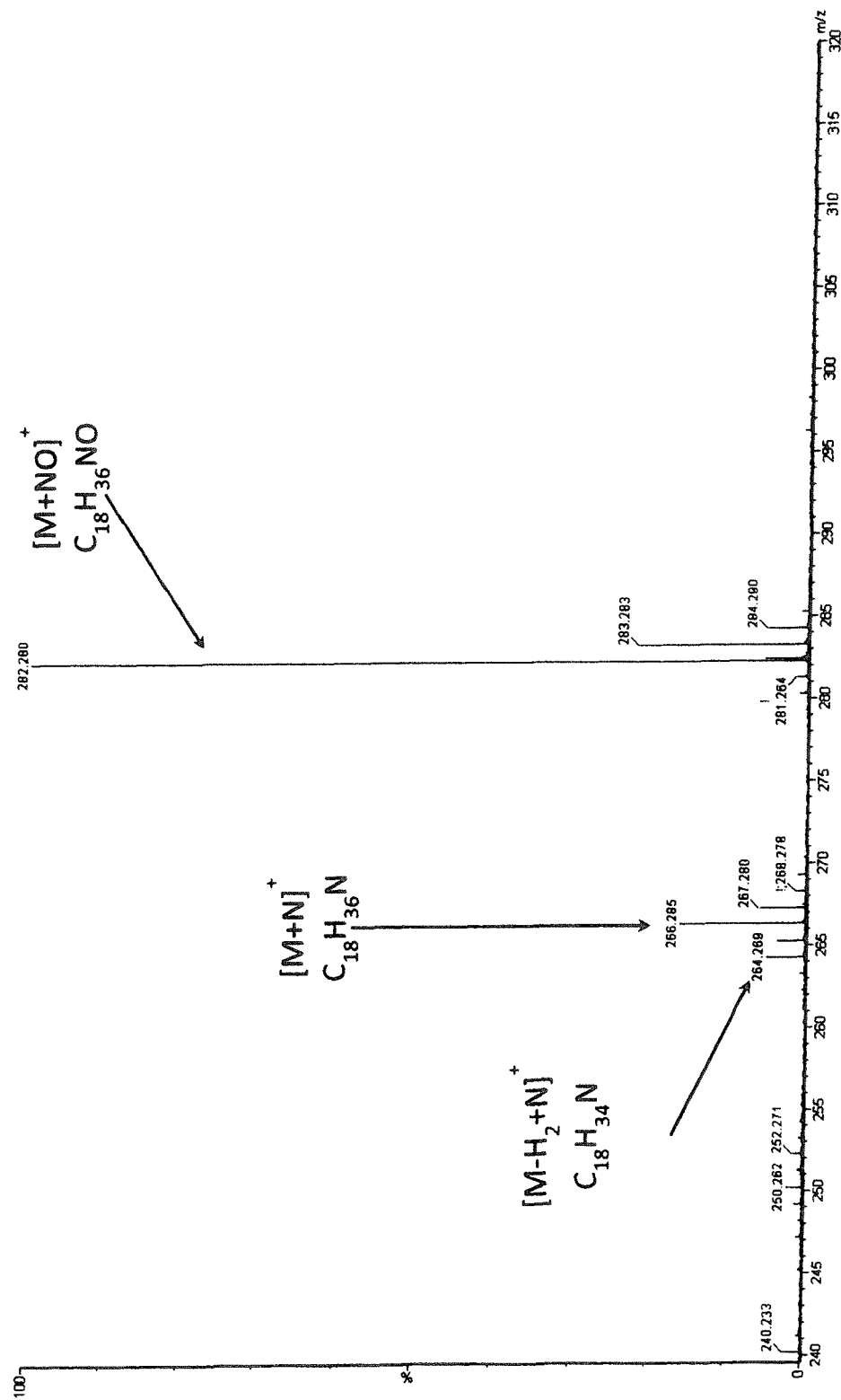
FIG. 6 shows a mass spectrum produced by APCI-GC analysis of 1-octadecene ($C_{18}H_{36}$) using a prior art atmospheric pressure chemical ionisation method.

Alkenes (olefins) have also been shown to produce adducts by a different process in a conventional charge transfer APCI-GC environment to that observed for alkanes (paraffins). FIG. 6 shows the spectrum produced from the APCI-GC analysis of 1-octadecene ($C_{18}H_{36}$) where an $[M+N]^+$ (M+14) adduct and a di-hydride abstracted nitrogen adduct $[M-H_2+N]^+$ (M+12) are seen in the first cluster, with the main base peak observed as the $[M+NO]^+$ (M+30) adduct. The ionisation process is similar for the alkane and alkene (FIGS. 5 and 6 respectively), but the alkane mass spectrum is dominated by the $[M+N]^+$ ion peak and has a much smaller $[M+NO]^+$ peak and a couple of other adduct peaks, while the alkene mass spectrum is dominated by the [M+NO]$^+$ ion peak and a much smaller [M+N]$^+$ adduct peak.

Example 5

Figure 7:
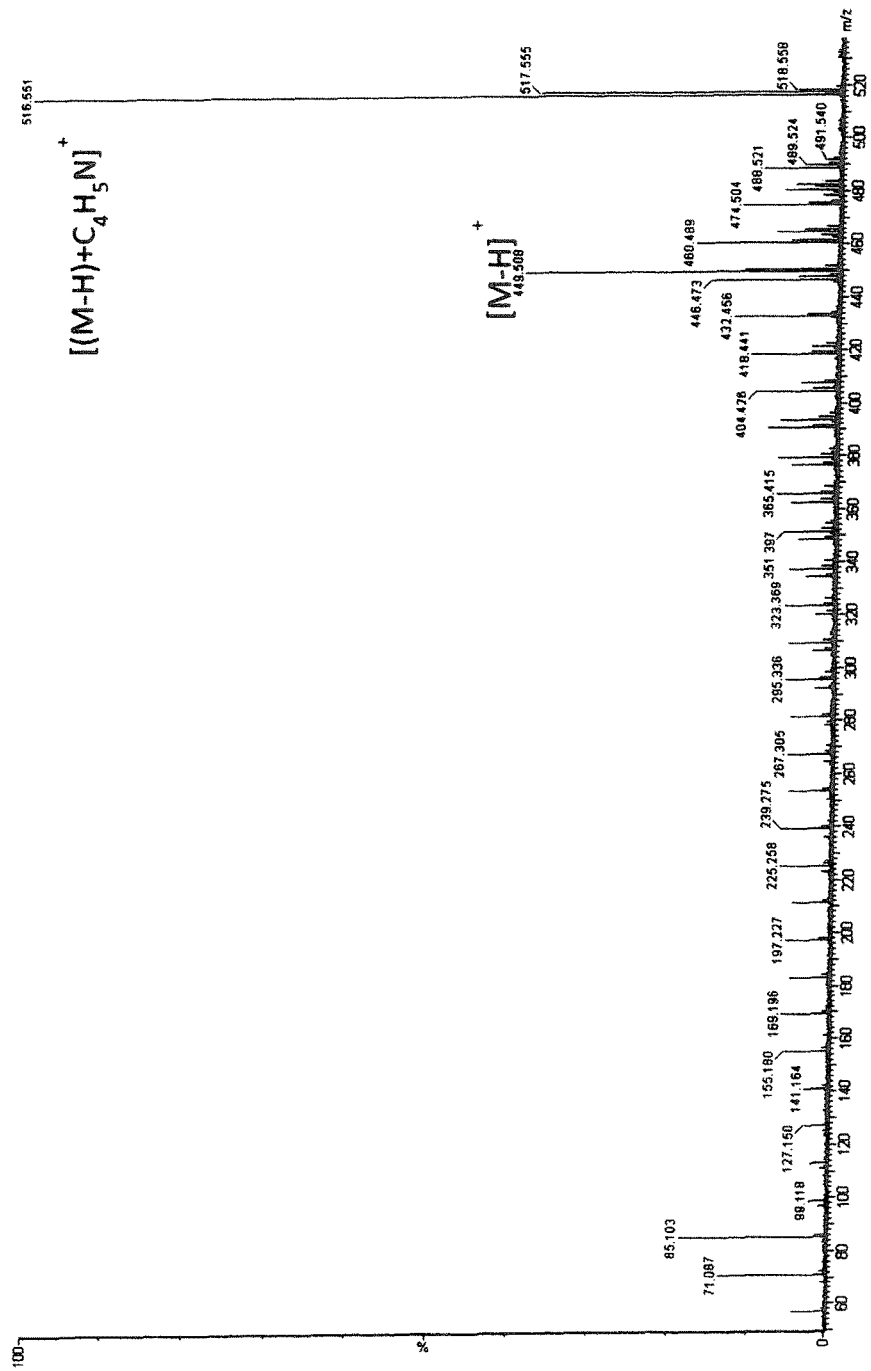
FIG. 7 shows a mass spectrum produced by APCI-GC analysis of the alkane dotriacontane ($C_{32}H_{66}$) according to the invention.

FIG. 7 shows the mass spectrum of the alkane dotriacontane ($C_{32}H_{66}$) produced via APCI-GC using pyrrole as a heterocyclic modifier. The dominant base peak in the spectrum is the [(M−H)+$C_4H_5N$]$^+$ (M+66) hydride abstracted pyrrole adduct. Additionally, there is the hydride abstracted [M−H]$^+$ (M−1) ion and structural information from the alkane backbone with the spectral peaks separated by 14 m/z ($CH_2$). A comparison with FIGS. 3 and 4 demonstrates the effect of the heterocyclic modifier on the resulting mass spectrum.

Example 6

Figure 8:
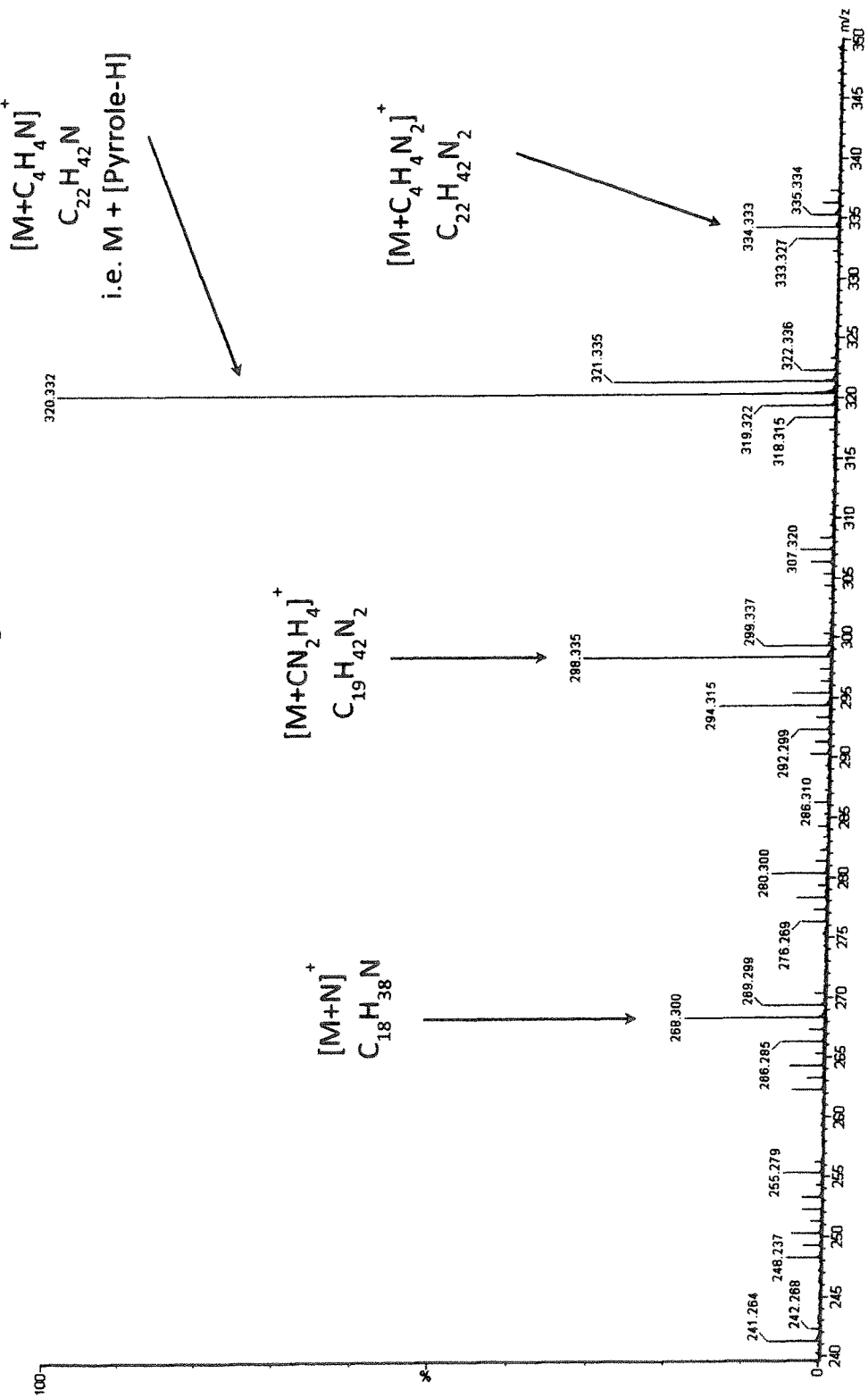
FIG. 8 shows a mass spectrum produced by APCI-GC analysis of the alkane octadecane according to the invention.

Shorter alkanes (e.g. $C_{18}H_{38}$) react with the heterocyclic modifier in a dominant adduction process with the pyrrole molecule, as seen in FIG. 8. Here the mass spectrum for octadecane using pyrrole as a modifier shows the [M+N]$^+$ (M+14) and [M+$CN_2H_4$]$^+$ (M+44) ions, but with the base peak being the hydride abstracted pyrrole adduct of octadecane [(M−H)+$C_4H_5N$]$^+$ (M+66), in addition to a small [M+$C_4H_4N_2$]$^+$ (M+80) peak. A comparison with FIG. 5 demonstrates the effect of the heterocyclic modifier on the resulting mass spectrum.

Example 7

Figure 9:
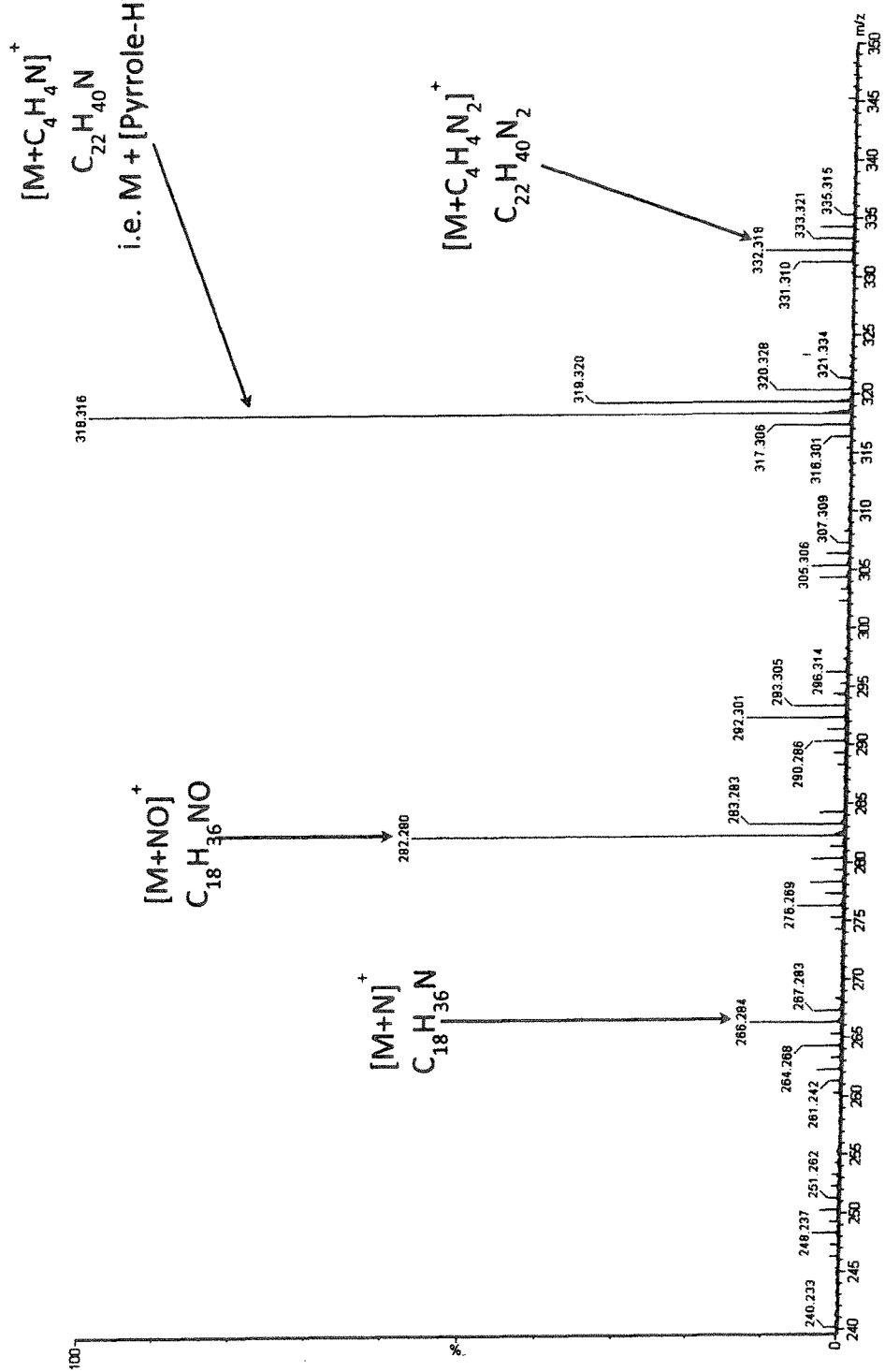
FIG. 9 shows a mass spectrum produced by APCI-GC analysis of the alkene 1-octadecene according to the invention.

Alkenes react with the heterocyclic modifier in the same way as alkanes, as seen in FIG. 9. Here the mass spectrum for 1-octadecene using pyrrole as a modifier shows the [M+N]$^+$ (M+14) and [M+NO]$^+$ (M+30) ions, but with the base peak being the pyrrole adduct of the hydride abstracted 1-octadecene [(M−H)+$C_4H_5N$]$^+$ (M+66), in addition to a small [M+$C_4H_4N_2$]$^+$ (M+80) peak. A comparison with FIG. 6 demonstrates the effect of the heterocyclic modifier on the resulting mass spectrum.

FIGS. 7, 8 and 9 show that the pyrrole adducted [M−H]$^+$ ion is consistently the base peak for both alkanes and alkenes, with alkynes and other associated multi-unsaturated aliphatic molecules expected to adduct in the same manner.

Example 8

Figure 10:
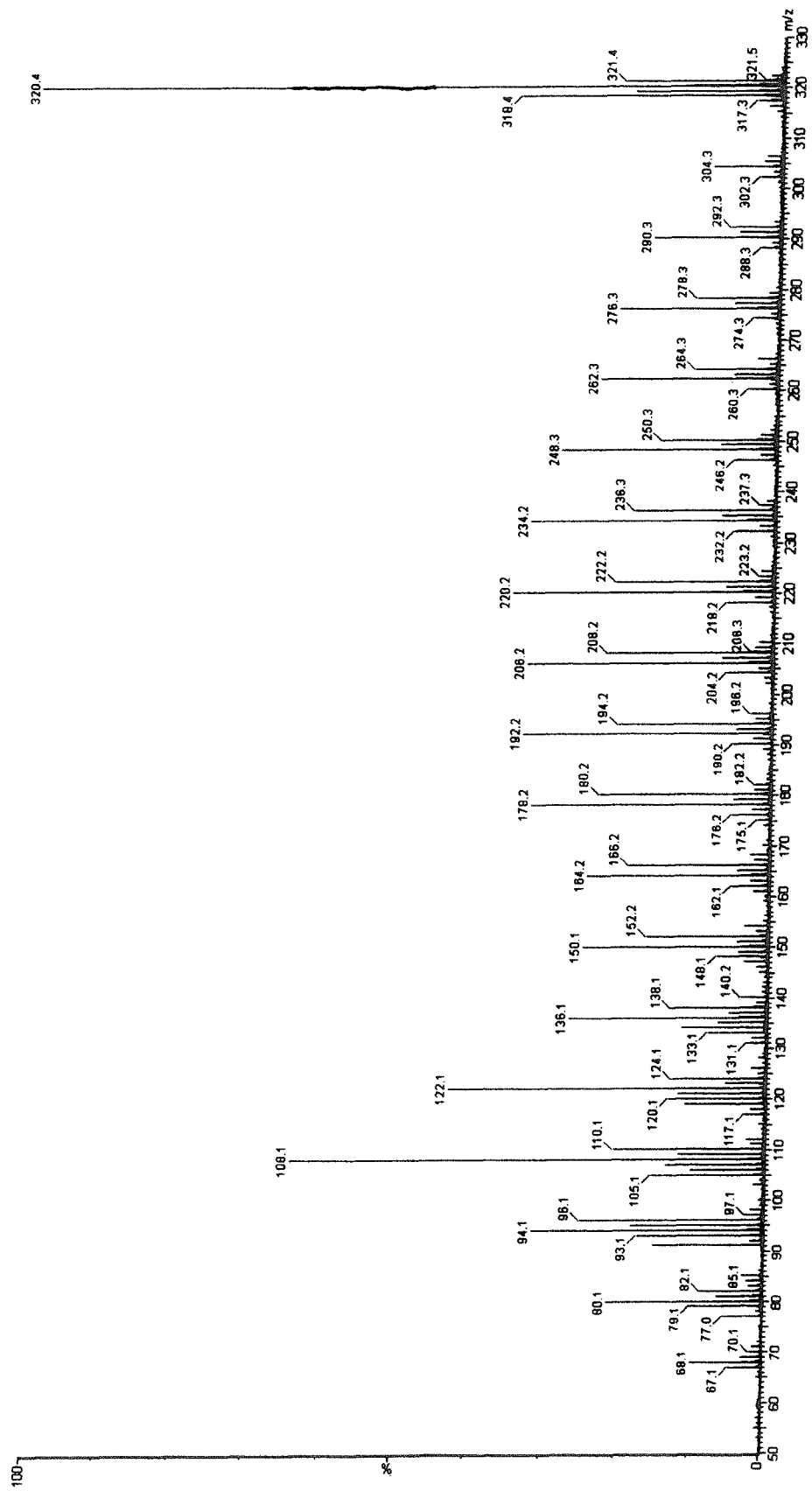
FIG. 10 shows a product ion spectrum produced by APCI-GC MS/MS analysis of the alkane octadecane according to the invention.

FIG. 10 was obtained using MS/MS and shows the product ion spectrum of the alkane octadecane ($C_{18}H_{38}$) with the hydride abstracted pyrrole adduct as the selected parent. The fragments produced are dominated by the progressive loss of $CH_2$ (14 m/z), which provides structural information for the adducted alkane analyte. The structural information could be used to determine the location of aliphatic branching and the position of double and triple bond sites.

Example 9

Figure 11:
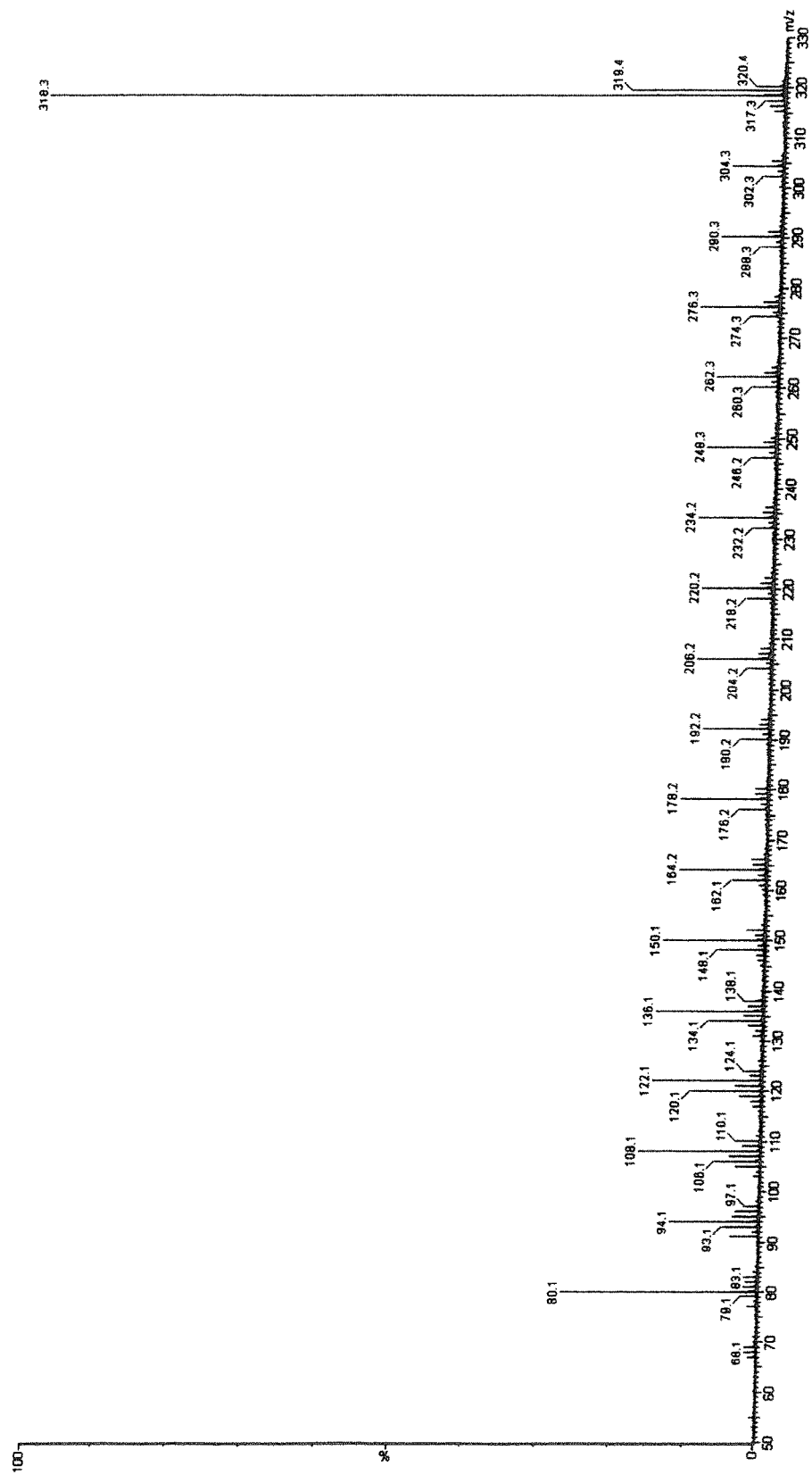
FIG. 11 shows a product ion spectrum produced by APCI-GC MS/MS analysis of the alkene 1-octadecene according to the invention.

FIG. 11 was obtained using MS/MS and shows the product ion spectrum of the alkene 1-octadecene ($C_{18}H_{36}$) with the hydride abstracted pyrrole adduct as the selected parent. The fragments produced are also dominated by the progressive loss of $CH_2$ (14 m/z) which can once again provide structural information of the adducted alkene analyte. The structural information could be used to determine the location of aliphatic branching and the position of double and triple bond sites.

The consistency of adduct formation for both alkanes and alkenes through the use of heterocyclic modifiers results in a simplified ionisation profile for these compounds resulting in a simplified method of identification. In addition, extra masses and fragmentation data is produced which assists in confirming the identity of the analyte.

The invention claimed is:

1. A method of mass spectral analysis of an aliphatic compound, comprising: ionizing the aliphatic compound in the presence of a heterocyclic compound.

2. The method of claim 1, wherein the ionisation process is atmospheric pressure chemical ionisation (APCI), atmospheric pressure photoionisation (APPI), or APCI/APPI mixed mode ionisation.

3. The method of claim 1, wherein the mass spectral analysis utilises GC-MS, LC-MS or SFC-MS.

4. A method of atmospheric pressure chemical ionisation mass spectrometry for gas chromatography (APCI-GC) of an aliphatic compound, comprising: performing the APCI-GC of the aliphatic compound in the presence of a heterocyclic compound.

5. A method for analysing an aliphatic compound by mass spectrometry which comprises:
   (i) ionising an aliphatic compound in the presence of a heterocyclic modifier; and
   (ii) mass analysing the resulting ions to obtain mass spectrometric data.

6. A method according to claim 5, wherein the ionisation is atmospheric pressure chemical ionisation, atmospheric pressure photoionisation or atmospheric pressure chemical ionisation/atmospheric pressure photoionisation mixed mode ionisation.

7. A method according to claim 5, further comprising subjecting the ions resulting from step (i) to ion mobility separation prior to mass analysing them.

8. A method according to claim 5, wherein the mass spectrometric data is compared with mass spectrometric data obtained without use of the heterocyclic modifier and/or with mass spectrometric data obtained using a different heterocyclic modifier.

9. A method according to claim 5, wherein the mass spectrometry is tandem mass spectrometry.

10. A method according to claim 5, wherein prior to ionisation the aliphatic compound is in effluent from a gas-chromatograph.

11. A method according to claim 5 wherein prior to ionisation the aliphatic compound is in effluent from a liquid-chromatograph.

12. A method according to claim 5 wherein prior to ionisation the aliphatic compound is in effluent from a supercritical fluid chromatograph.

13. A method according to claim 5 wherein the mass spectrometry is atmospheric pressure chemical ionisation mass spectrometry for gas chromatography.

14. A method according to claim 5 wherein the aliphatic compound is a linear or branched chain hydrocarbon.

15. A method according to claim 5 wherein the aliphatic compound is an alkane, alkene or alkyne, or a mixture thereof.

16. A method according to claim 5 wherein the aliphatic compound is a hydrocarbon containing 5 or more carbon atoms.

17. A method according to claim 5 wherein the aliphatic compound is a $C_5$ to $C_{120}$ hydrocarbon.

18. A method according to claim 5 wherein the aliphatic compound is comprised in crude oil or a fraction thereof.

19. A method according claim 5 wherein the heterocyclic modifier is a mono-, bi- or tricyclic heterocyclic compound containing carbon atoms and 1-4 heteroatoms.

20. A method according to claim 19, wherein the heteroatoms are selected from oxygen, sulphur and/or nitrogen.

21. A method according to claim 5 wherein the heterocyclic modifier is monocyclic.

22. A method according to claim 5 wherein the heterocyclic modifier is aromatic.

23. A method according to claim 5 wherein the heterocyclic modifier is selected from oxetane, azetidine, thietane, pyrrole, furan, tetrahydrofuran, thiophene, tetrahydrothiophene (thiolane, thiophane), indole, benzothiophene, benzofuran (coumarone), dioxane, piperazine, thiane, dithiane, pyrrolidine, pyridine, pyrimidine, pyrazine, pyran, thiopyran, piperadine, tetrahydropyran, imidazoline, imidazole, pyrazole, oxazole, thiazole, isoxazole, triazole, tetrazole, quinoline, isoquinoline, purine, dibenzofuran and dibenzothiophene, and alkylated derivatives thereof.

24. A method according to claim 5 wherein the heterocyclic modifier is pyrrole.

* * * * *